United States Patent [19]

Szabo et al.

[11] 4,044,764
[45] Aug. 30, 1977

[54] FLUID INFUSION APPARATUS

[76] Inventors: Anthony W. Szabo, 37 Cobblewood Road, Livingston, N.J. 07039; Louis R. M. Del Guercio, 14 Pryer Lane, Larchmont, N.Y. 10538

[21] Appl. No.: 627,341

[22] Filed: Oct. 30, 1975

[51] Int. Cl.² .......................................... A61M 5/20
[52] U.S. Cl. ...................... 128/214 F; 128/DIG. 12
[58] Field of Search ........... 128/214 D, 214 F, 214 E, 128/DIG. 12, DIG. 13, DIG. 1, 218 A, 218 F; 74/200, 380; 269/249, 97; 222/102, 333

[56] References Cited

U.S. PATENT DOCUMENTS

| 673,424 | 5/1901 | Denton | 74/380 |
|---|---|---|---|
| 2,422,306 | 6/1947 | Laing | 74/200 X |
| 2,550,537 | 4/1951 | Derrick | 222/102 |
| 2,602,446 | 7/1952 | Glass et al. | 128/218 A |
| 2,669,832 | 2/1954 | Harris et al. | 74/380 X |
| 2,686,614 | 8/1954 | Geressy et al. | 222/102 |
| 2,764,980 | 10/1956 | Smith | 128/218 A |
| 2,786,468 | 3/1957 | Singer et al. | 128/218 A |
| 2,849,896 | 9/1958 | Lappin et al. | 74/380 X |
| 3,017,174 | 1/1962 | Reuter | 269/97 |
| 3,151,616 | 10/1964 | Selfon | 128/214 F |
| 3,198,385 | 8/1965 | Maxwell | 128/214 F |
| 3,228,617 | 1/1966 | Roberts | 74/200 X |
| 3,240,078 | 3/1966 | Newell | 74/200 |
| 3,279,653 | 10/1966 | Pfleger | 128/DIG. 1 |
| 3,415,419 | 12/1968 | Jewett et al. | 128/218 A |
| 3,631,847 | 1/1972 | Hobbs | 128/218 A |
| 3,701,345 | 10/1972 | Heilman et al. | 128/DIG. 1 |
| 3,720,211 | 3/1973 | Kyrias | 128/218 A |
| 3,738,533 | 6/1973 | Bertrand | 222/102 |
| 3,858,581 | 1/1975 | Kamen | 128/218 A |
| 3,880,138 | 4/1975 | Wootten | 128/214 F |
| 3,884,228 | 5/1975 | Hahn | 128/DIG. 12 |
| 3,886,938 | 6/1975 | Szabo | 128/214 F |

FOREIGN PATENT DOCUMENTS 28,796  6/1914  United Kingdom ............ 128/218 A

Primary Examiner—Russell R. Kinsey
Assistant Examiner—Paul J. Hirsch
Attorney, Agent, or Firm—Larson, Taylor and Hinds

[57] ABSTRACT

A portable, automatic fluid infusion apparatus is presented for the administration to an ambulatory patient of a predetermined amount of fluid at an adjustable, predetermined rate over an extended time period. A feature of the invention is a soft plastic bag from which the predetermined amount of fluid is dispensed.

5 Claims, 6 Drawing Figures

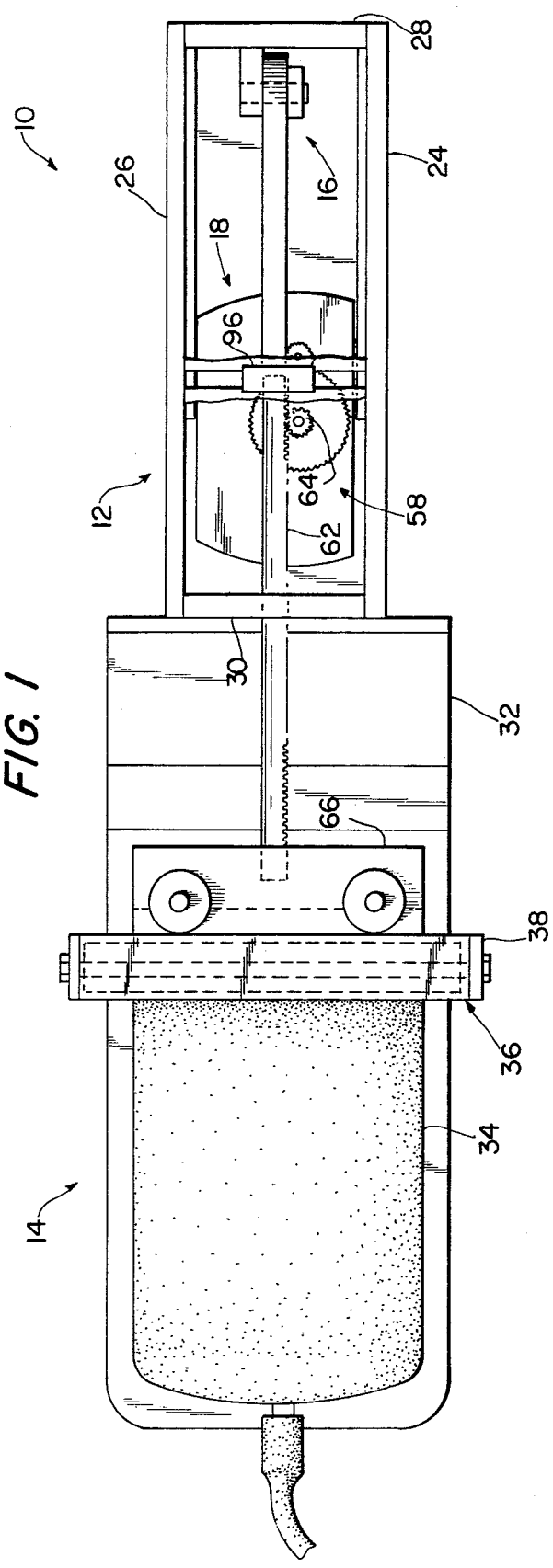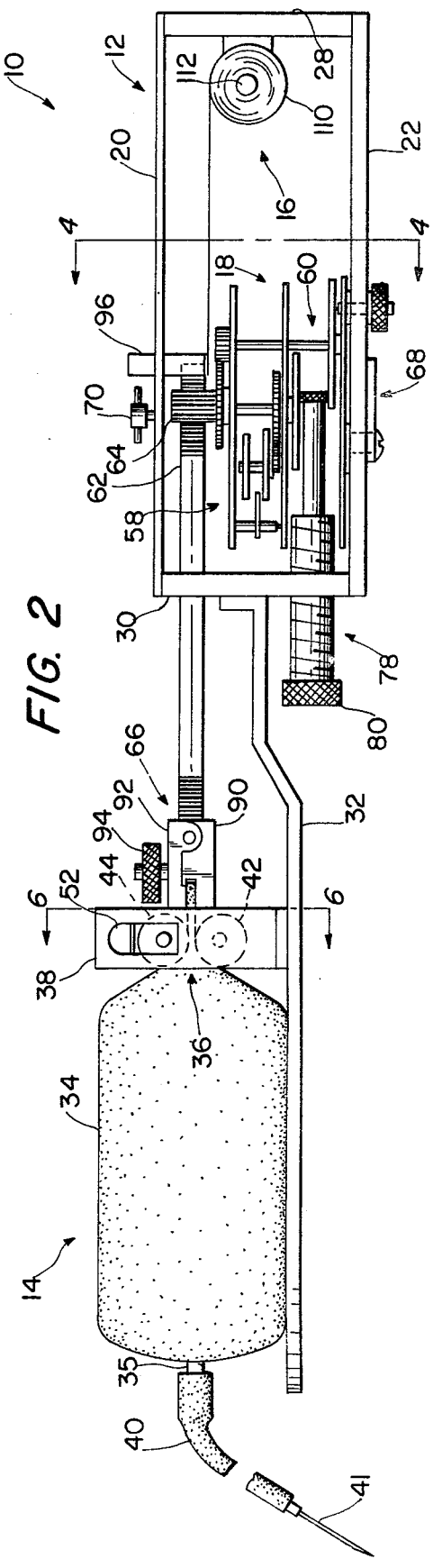

FLUID INFUSION APPARATUS

FIELD OF THE INVENTION

This invention relates to fluid infusion devices and, more particularly, to automatic infusion devices that can be adjusted to allow a desired rate of fluid to infuse into a ambulatory patient.

BACKGROUND OF THE INVENTION

The general background of infusion devices can be found in Szabo et al., U.S. Pat. No. 3,886,938, and in Szabo et al., copending U.S. application Ser. No. 579,232 which issued to U.S. Pat. No. 3,993,065.

As can be seen from the above noted prior art, a variety of infusion arrangements have been proposed to meet the problems associated with the infusion of fluid into an ambulatory patient. A disadvantage of these devices is that the basic power and timing mechanism is only incorporable into one infusion apparatus configuration. Thus, though one of these devices might be easily mountable to one portion of a patient's body, it might not be so easily mountable to another. Consequently, different types of devices with different power mechanisms specifically adaptable to the various bodily configuration would have to be stocked and maintained.

Also there are times when it is desirable to be able to disengage the power and timing mechanisms from the receptacle which stores the fluid to be infused. Such a need arises when the receptacle is initially filled, and when it becomes desirable during the actual infusion process to interrupt that process. Thus this disengaging ability could be used to, for example, temporarily discontinue the fluid administration without disconnecting the device from the patient, or to enable the fluid to be manually administered.

Further, prior art devices generally lack the ability to store and administer large quantities of a fluid, as for example, required for the administration of blood.

Finally, prior devices have, in general, lacked a speed control to adjust the rate at which fluid is infused into a patient. Such a control to be used effectively must be simple in operation and design.

SUMMARY OF THE INVENTION

The present invention provides for a fluid infusion apparatus that is portably attachable to a patient for the administration of a predetermined amount of fluid at an adjustable, predetermined rate over an extended time period. This device has a basic power and timing mechanism which can be incorporated into a variety of infusion apparatus configurations, allowing standardization in operation and maintenance.

Also the basic power and timing mechanism can be readily disengaged from the fluid receptacle to, for example, temporarily interrupt the infusion process, to manually administer the fluid, or to fill the receptacle.

This device also incorporates therein an easily adjustable speed control that can readily change the rate at which fluid is infused into a patient. Further this invention has the ability to store and administer large quantities of fluid.

In accordance with a preferred embodiment of the invention, a fluid infusion apparatus capable of administering a predetermined amount of fluid at an adjustably predetermined rate over an extended time period is provided. The apparatus comprises in part an elongated housing attachable to a patient, a receptacle for storing the fluid to be infused, a power mechanism, and a timing mechanism. The timing mechanism further includes a main spring, an escapement mechanism and a control to vary the rate at which the fluid is administered. The control is manually operable and includes a main driving disc engaged by the main spring, a driven disc, a wheel for placing the driving disc in mechanical communication with the driven disc, and a shaft onto which the wheel is rotatably mounted. The rotation of the shaft about its longitudinal axis positions the wheel along the radii of both the driving and the driven discs and thus varies the speed at which the driving disc turns the driven disc.

Additional features and advantages of the invention will be set forth in, or apparent from, the detailed description of preferred embodiments of the invention found hereinbelow.

BRIEF DESCRIPTION OF THE DRAWINGS

FIG. 1 is a plan view of the presently preferred embodiment of the invention wherein one side of the housing has been removed for illustrating the internal parts thereof;

FIG. 2 is a front elevation view of the embodiment shown in FIG. 1, wherein one side of the housing has been removed for illustrating the internal parts thereof;

DETAILED DESCRIPTION OF THE PREFERRED EMBODIMENTS

Figure 4:
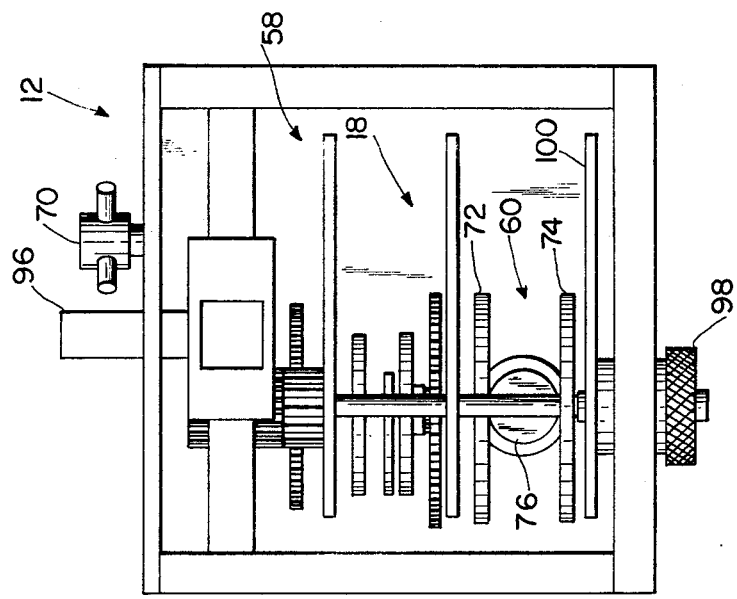
FIG. 4 is an enlarged transverse cross-sectional view taken along line 4—4 of FIG. 2.

With reference to the Figures and, in particular, to FIGS. 1 and 2, a presently preferred embodiment of a fluid infusion apparatus 10 is shown in accordance with the invention. For purposes of discussion, fluid infusion apparatus 10 can conveniently be separated into the following functional units: housing 12, dispensing mechanism 14 for storing and dispensing the fluid, mountable to the outside of housing 12, power mechanism 16, and timing movement 18.

As can best be seen in FIGS. 1 and 2, housing 12 comprises a rectangular structure that includes top 20, bottom 22, sides 24 and 26, and ends 28 and 30, which are preferably bolted together. Housing 12 is preferably constructed of a light metallic material such as, for example, aluminum. Further, housing 12 can be fitted with a set of straps (not shown) so that apparatus 10 can be mounted onto a patient.

Figure 6:
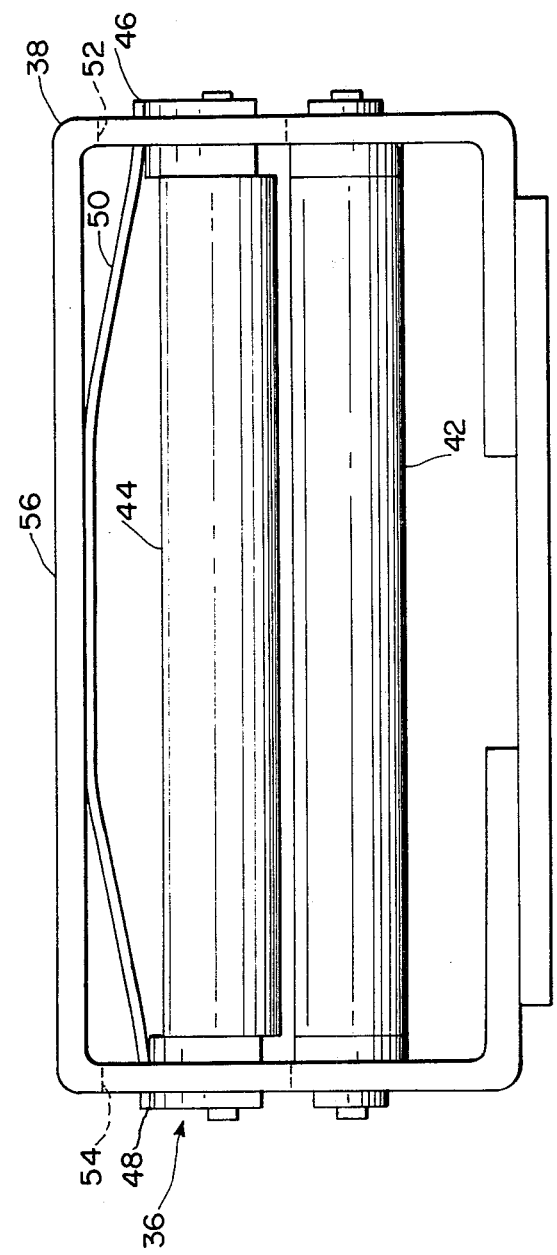
FIG. 6 is an enlarged transverse cross-sectional view taken along line 6—6 of FIG. 2.

Dispensing mechanism 14 (FIGS. 1 and 2) which is the next functional unit to be discussed, is mounted to housing 12 by mounting bracket 32. Mechanism 14 principally comprises a flexible receptacle 34 with a dispensing end 35, a flexible conduit 40 mounted to dispensing end 35 with a hypodermic needle 41 mounted onto conduit 40, a set of elongate rollers 36 (FIG. 6) through which receptacle 34 is pulled, a spring 50 (FIG. 6) for urging roller set 36 together about receptacle 34, and a second mounting bracket 38 for mounting roller set 36, bracket 38 fixedly attached to bracket 32.

Generally dispensing mechanism 14 is designed so that fluid stored in receptacle 34 is dispensed through end 35 as receptacle 34 is pulled through roller set 36. A detailed description of the components of dispensing mechanism 14 follows.

Flexible receptacle 34, which is one of the main components of dispensing mechanism 14, can be constructed of, for example, a soft plastic material that would not react with the fluid dispensed therefrom and that would not crack or rupture on being pulled through rollers 36.

Elongate rollers 36 (FIG. 6) which is another component of dispensing mechanism 14, include lower roller 42 and upper roller 44. Lower roller 42 is rotatably mounted in bracket 38. Upper roller 44 is provided with a central supporting shaft 43 having its end portions journalled in bearings 46 and 48 which are slidably mounted in slots 52 and 54 of bracket 38 with the end portions of spring 50 engaging bearings 46 and 48 to urge roller 44 towards the ends of slots 52 and 54 and thus adjacent to roller 42. Spring 50 is further fixedly attached to a side 56 of bracket 38 adjacent to roller 44. With spring 50 in an uncompressed state, rollers 36 contact each other. After receptacle 34 is placed between roller set 36, rollers 42 and 44 become spaced apart by no more than a distance approximately equal to twice the thickness of the material of receptacle 34. As fluid filled receptacle 34 is pulled through roller set 36, rollers 42 and 44 rotate in bracket 38. Simultaneously, spring 50 urges roller 44 against receptacle 34 and roller 42 so that the fluid in receptacle 34 is always kept between rollers 36 and dispensing end 35. It would be undersirable for fluid in receptacle 34 to pass through rollers 36 since this would invalidate the predetermined fluid infusion rate.

Dispensing end 35 of receptacle 34 is preferably integrally molded with or fixedly attached to receptacle 34. End 35 provides a semi-rigid tube like member over which an end of flexible conduit 40 may be stretched. Needle 41 is removably attached to the distal end of conduit 40 so that fluid contained in receptacle 34 flows through end 35, conduit 40 and needle 42 as power mechanism 16 and timing movement 18 cooperate to pull receptacle 34 through rollers 36.

Figure 3:
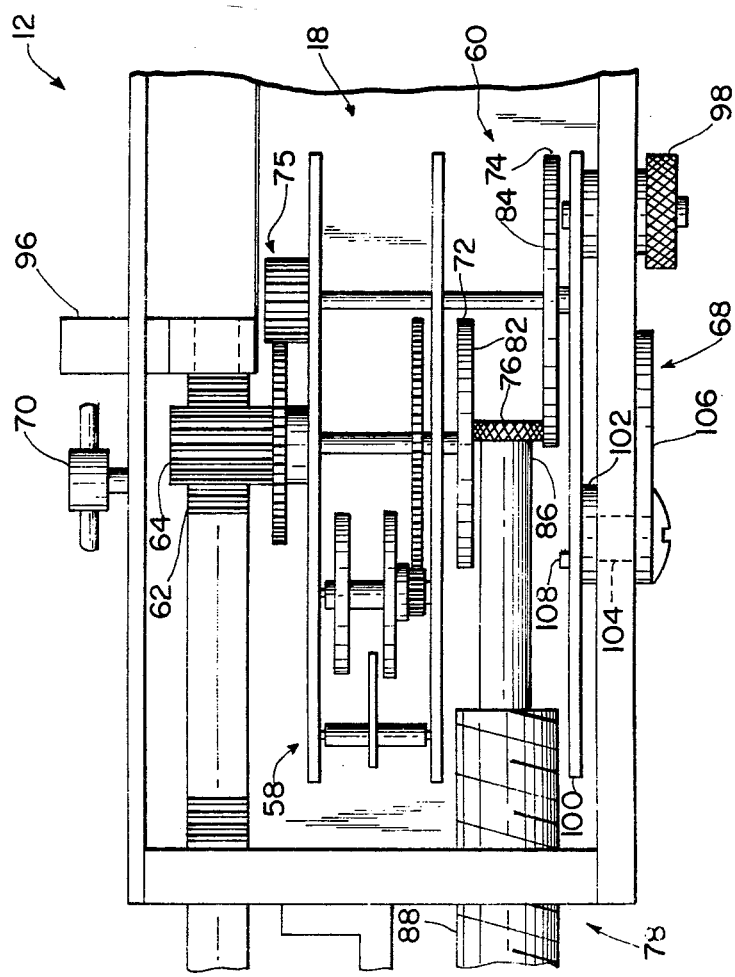
FIG. 3 is an enlarged front elevation view of the internal parts of the device depicted in FIG. 2.

Timing movement 18 (FIGS. 1,2,3,4), the next functional unit to be discussed, principally comprises a spring wind clock motor 58 with a variable speed control 60 and a pivotal mount 68 for motor 58. Spring wind clock motor 58 is a standard horological instrument. It includes a spring winder knob 70 (shown in FIG. 3 disconnected from motor 58), an escapement mechanism, and a gearing network which activates a main driving disc 72 (FIGS. 3,4). Disc 72, consequently, rotates at a constant speed as fixed by the gearing network of clock motor 58.

Figure 5:
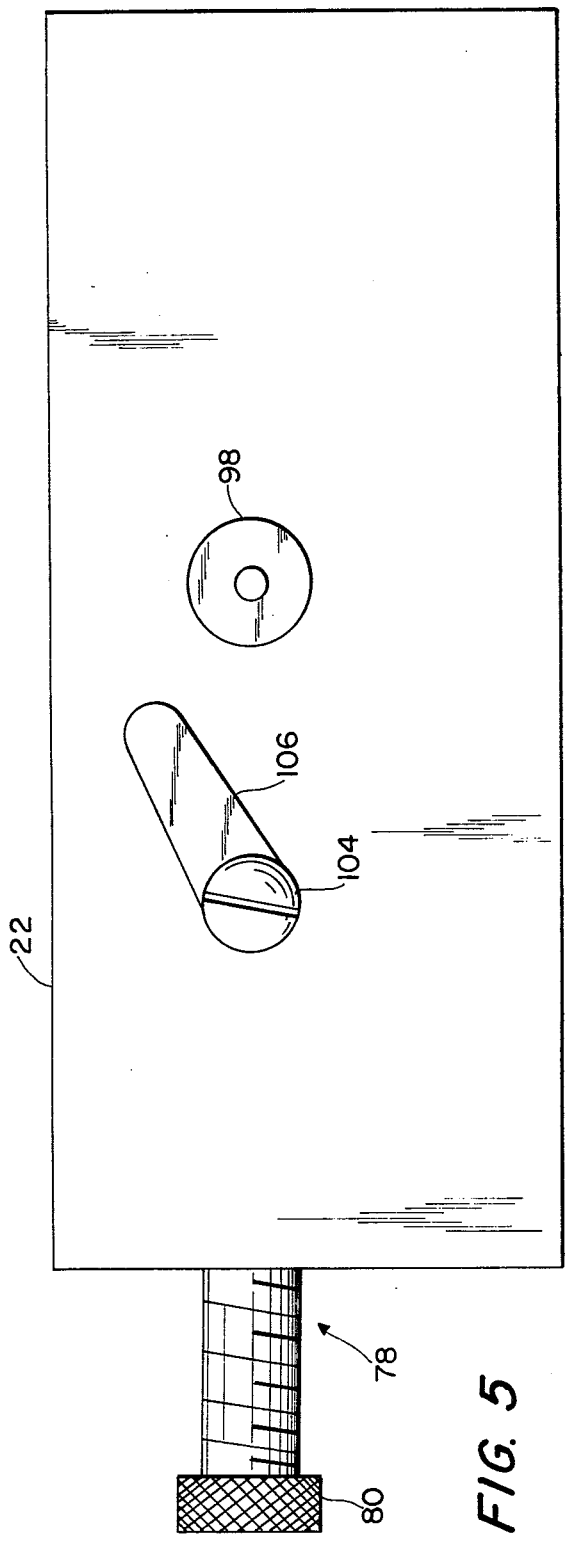
FIG. 5 is an enlarged bottom view of the housing as depicted in FIG. 2.

Variable speed control 60 is operatively connected with driving disc 72 so that timing mechanism 18 can be adjusted to vary the rate of infusion. Control 60 includes a driven disc 74 (FIGS. 3 and 4), a wheel 76 for placing driving disc 72 into mechanical communication with driven disc 74, and partially threaded shaft 78 onto which wheel 76 is rotatably mounted. Driving disc 72 and driven disc 74 are essentially parallel, with wheel 76 being essentially perpendicular to both. Wheel 76 contacts both face 82 of disc 72 and face 84 of disc 74, face 82 being juxtaposed to face 84. Wheel 76 is mounted onto the end of unthreaded portion 86 of shaft 78. It is mounted such that its axis of rotation is coincident with the axis of shaft 78. Threaded portion 88 of shaft 78 is received by a threaded bore located on housing end wall 30. A knurled knob 80 (FIG. 5) is fixedly attached to the end of threaded portion 88 of shaft 78 distally from wheel 76. As knob 80 is rotated, shaft 78 moves along its longitudinal axis into or out of the threaded bore, causing wheel 76 to move along the radii of discs 72 and 74. As disc 72 and 74 do not have a coincident axis of rotation and as wheel 76 causes driving disc 72 to rotate driven disc 74, the movement of wheel 76 along the aforementioned radii varies the speed at which disc 72 drives disc 74.

Driven disc 74 is connected to a pinion 64 by a set of gears generally denoted 75 (FIG. 3). Pinion 64 is, in turn, in mechanical communication with a rack 62. Thus control 60 varies the speed at which motor 58 drives pinion 64, and thus the speed at which pinion 64 drives rack 62. Rack 62 slidably projects through an aperture in end wall 30 of housing 12. Gripper jaws 66 (FIG. 2) are fixedly attached to the end of that portion of rack 62 which extends out of housing 12. Gripper jaws 66 engage the end portion of receptacle 34 located distally from end 35 and pull receptacle 34 through roller 36. Further, gripper jaws 66 include a lower stationary jaw 90 fixedly attached at one end thereof to rack 62 (FIG. 2), and upper jaw 92 pivotally attached at one end thereof to jaw 90, and a locking screw 94 which when rotated tightens the free ends of jaws 90 and 92 about the aforementioned end portion of receptacle 34.

At the end of rack 62, located inside housing 12, is a slider finger 96 (FIGS. 1,2,3,4). Slider finger 96 projects through a longitudinal slot (not shown) in top 20 of housing 12. Using slider finger 96, rack 62 may be manually positioned relative to pinion 64, when pinion 64 has been disengaged from rack 62, so that jaws 66 are in a proper position to engage the end of receptacle 34.

To allow pinion 64 to be disengaged from rack 62, clock motor 58, variable speed control 60, except for shaft 78 and wheel 76, and pinion 64 are pivotally mounted to the inside of bottom 22 of housing 12 by mount 68. Pivotal mount 68 includes a knurled handled lock nut 98 (FIG. 3) mounted on the outer surface of bottom 22 of housing 12 for lockingly positioning motor 58, a first lever arm 100 fixedly attached to motor 58 and pivotable about the axis of lock nut 98, a flat eccentric disk 102 rotatably mounted adjacent the inner surface of bottom side 20 on the end of a shaft 104 that extends through an aperture in bottom 20 of housing 12, and a second lever 106, fixedly attached to shaft 104, adjacent the outer surface of bottom side 20. First lever arm 100 is rotatably pinned by pin 108 to eccentric disk 102 but out of axial alignment with shaft 104. Consequently, when nut 98 is turned releasing clock motor 58 from a fixed position relative to housing 12, a rotation of second lever 106 about the axis of rotation of shaft 104 causes eccentric disc 102 to pivot first lever arm 100 about the axis of lock nut 98. As first lever 100 pivots about nut 98, clock motor 58 also pivots thereabout and thus pioion 64 swings out of mechanical engagement with rack 62.

Finally, mounted to the inside of end wall 28 of housing 12 (FIGS. 1 and 2), is power mechanism 16. Mechanism 16 assists timing movement 18 in pulling rack 62 into housing 12 and thus receptacle 34 through rollers 36. Power mechanism 16 includes a spring 110 wound in concentric circles about a mounting bracket 112. The free end of spring 110 is fixedly attached to slider finger 96 which, as heretofore discussed, is mounted on an end of rack 62. If pinion 64 were disengaged from rack 62, spring 110 would immediately pull rack 62 into housing 12. Consequently, when rack 62 engages pinion 64, power mechanism 16 assists timing movement 18 in pulling rack 62 into housing 12 and timing movement 18 regulates the speed at which rack 62 enters housing 12.

The operation of fluid infusion apparatus 10 is as follows. Nut 98 is loosened and clock motor 58 is pivoted about the axis of nut 98 so that pinion 64 becomes disengaged from rack 62. Thus slider finger 96 and thus rack 62 and gripper jaws 66 can be manually positioned. A fluid filled receptacle 34 is placed on bracket 32 and one end thereof is fed through roller 36. Slider finger 96 is positioned so that gripper jaws 66 can lockingly engage the end of receptacle 34 fed through rollers 36. The speed at which receptacle 34 is to be pulled through rollers 36 and thus the rate of fluid infusion into a patient is set by adjusting knurled knob 80. Clock motor 58 is then pivoted so that pinion 64 again engages rack 62 and is locked in place relative to housing 12 by the tightening of nut 98. Then apparatus 10 is strapped to a patient at a desired location. Thereafter timing movement 18 and power mechanism 16 pull receptacle 34 through rollers 36 and fluid is dispensed from receptacle 34 through needle 41 at a set fixed rate. At any time durting the infusion operation, the rate of infusion can be changed by adjusting knurled knob 80. Also the infusion rate can be interrupted by disengaging pinion 64 from rack 62 and thereby disengaging receptacle 34 from timing movement 18. At this point fluid can also be infused into a patient by manually pulling slider finger 96 so as to bring rack 62 into housing 12.

Besides the previously discussed embodiment of the invention, several alternative embodiments are here presented. These embodiments vary from the above described embodiment as to the configuration of dispensing mechanism 14.

The first of the alternative embodiments (not shown) has a dispensing mechanism similar to that discussed in previously referenced U.S. Pat. No. 3,993,065 issued to Szabo et al., which is hereby incorporated by reference. This embodiment includes a syringe which is operated by a flexible coaxial cable, the outer casing of which flexibly connects the syringe housing to housing 12, and the inner rod of which flexibly connects the plunger of the syringe to rack 62. However, in this embodiment rack 62 is arranged so that it can push the rod through the casing and thus push the plunger through the syringe housing thereby dispensing fluid therefrom.

The second alternative embodiment (not shown) has a dispensing mechanism similar to that discussed in previously referenced U.S. Pat. No. 3,886,938 issued to Szabo et al., which is hereby incorporated by reference. In this embodiment an end of the syringe housing is fixedly attached to an end wall of housing 20 and the plunger of the syringe is fixedly attached to rack 62 such that the syringe and rack 62 are coaxially alligned. Again, in this embodiment rack 62 is arranged so that it can push the plunger through the syringe housing, thereby dispensing fluid therefrom.

The third alternative embodiment (not shown) has a dispensing mechanism similar to that discussed in U.S. Pat. No. 3,415,419 issued to Jewett, which is hereby incorporated by reference, and in British Patent Specification No. 1,026,593. In this embodiment the length of the syringe housing is fixedly attached to a longitudinal side wall of housing 12. A bracket mounted at the end of rack 62 engages the plunger of the aforementioned syringe. Rack 62 and the plunger describe parallel paths as the rack pushes the plunger into the syringe housing, thereby forcing fluid to be dispensed from the syringe.

Although the invention has been described with respect to an examplary embodiment thereof, it will be understood by those of ordinary skill in the art that variations and modifications may be effected within the scope and spirit of the invention.

We claim:

1. Portable, automatic fluid infusion apparatus for administering a predetermined amount of fluid at an adjustable, predetermined rate over an extended time period, the device comprising:
    an elongated housing attachable to a patient;
    a mechanical power means including a main spring enclosed by said elongated housing, said infusion apparatus including an elongated member extendable from a first end of said housing and in axial alignment with said elongated housing, said power means further including a timing mechanism, said timing mechanism including an escapement mechanism and a control mechanism to adjust the rate at which the fluid is administered, wherein said control mechanism includes a main driving disc operably engaged by said main spring, a driven disc operably engageable with said elongated member, a wheel for placing said driving disc in mechanical communication with said driven disc, and a shaft onto which said wheel is rotatably mounted for positioning said wheel along the radii of both said driving and said driven discs, for varying the speed at which the driving disc turns the driven disc; and
    a receptacle means for storing the fluid, said receptacle means mounted at said first end of said housing in axial alignment therewith, said receptacle means including a soft plastic bag for holding the fluid, and a support platform for said soft plastic bag, said support platform fixedly attached to said first end of said elongated housing and in axial alignment therewith, said soft plastic bag positioned on said support platform in axial alignment with said elongated housing, said receptacle means further including a set of rollers fixedly attached to said support platform at a position adjacent said first end of said elongated housing, said soft plastic bag positioned between said set of rollers, said elongated member having a connecting means secured thereto for connecting said plastic bag to said elongated member, said elongated member for pulling said soft plastic bag through said rollers.

2. Infusion apparatus in accordance with claim 1 wherein said power means further includes a self-recoiling spring mounted to an interior surface of a second end of said elongated housing, said spring fixedly attached to said elongated member.

3. Infusion apparatus in accordance with claim 1 wherein said rollers include a roller that is rotatably mounted on fixed bearings and roller that is rotatably mounted on spring loaded floating bearings.

4. Infusion apparatus in accordance with claim 1 wherein said mechanical power means is pivotally mounted inside said housing so that said timing mechanism can be pivotally disengaged from said elongated member.

5. Infusion apparatus in accordance with claim 4 further including a manual control lever secured to said elongated member for dispensing fluid from said receptacle means when said timing mechanism power means is disengaged from said elongated member.

* * * * *